United States Patent
Breisacher

(10) Patent No.: US 10,267,624 B2
(45) Date of Patent: Apr. 23, 2019

(54) SYSTEM AND METHOD FOR RECONSTRUCTING A TRAJECTORY OF AN OPTICAL FIBER

(71) Applicant: Stryker European Holdings I, LLC, Kalamazoo, MI (US)

(72) Inventor: Jochen Breisacher, Teningen (DE)

(73) Assignee: STRYKER EUROPEAN HOLDINGS I, LLC, Kalamazoo, MI (US)

(*) Notice: Subject to any disclaimer, the term of this patent is extended or adjusted under 35 U.S.C. 154(b) by 423 days.

(21) Appl. No.: 14/974,724

(22) Filed: Dec. 18, 2015

(65) Prior Publication Data
US 2016/0178357 A1    Jun. 23, 2016

(30) Foreign Application Priority Data
Dec. 23, 2014  (EP) .................................. 14004396

(51) Int. Cl.
| | |
|---|---|
| *G01B 11/24* | (2006.01) |
| *A61B 34/20* | (2016.01) |
| *G01B 11/02* | (2006.01) |

(52) U.S. Cl.
CPC .............. *G01B 11/24* (2013.01); *A61B 34/20* (2016.02); *G01B 11/02* (2013.01); *A61B 2034/2061* (2016.02)

(58) Field of Classification Search
CPC ............ A61B 34/20; A61B 2034/2055; A61B 2034/2057; A61B 2034/2059;
(Continued)

(56) References Cited

U.S. PATENT DOCUMENTS

| | | | |
|---|---|---|---|
| 4,930,494 A |   | 6/1990 | Takehana et al. |
| 5,957,833 A | * | 9/1999 | Shan .................... A61B 1/31 600/117 |

(Continued)

FOREIGN PATENT DOCUMENTS

| | | |
|---|---|---|
| DE | 10100739 A1 | 8/2002 |
| DE | 102011017622 B3 | 10/2012 |

(Continued)

OTHER PUBLICATIONS

European Search Report for European Application No. EP 14 004 396.9 dated Jun. 22, 2015; 3 pages.

(Continued)

*Primary Examiner* — Gordon J Stock, Jr.
(74) *Attorney, Agent, or Firm* — Howard & Howard Attorneys PLLC

(57) ABSTRACT

A system for reconstructing a trajectory of an optical fiber is described. The system comprises an optical fiber to be inserted into an object, wherein the optical fiber has a length and at least one bending sensor unit arranged along its length. The system also comprises a measurement device configured to measure insertion length increments of the optical fiber and an interrogation device configured to detect optical feedback signals from the at least one bending sensor unit. The system further comprises a processor device configured to reconstruct the trajectory of the optical fiber along its inserted length using data pairs which are based on measured insertion length increments and detected optical feedback signals assigned thereto. Furthermore, a method for reconstructing the trajectory of the optical fiber and a computer program product for executing the method are described.

22 Claims, 6 Drawing Sheets

(58) Field of Classification Search
CPC .... A61B 2034/2061; A61B 2034/2065; A61B 2034/2072; G01B 11/02; G01B 11/04; G01B 11/043; G01B 11/16; G01B 11/161; G01B 11/165; G01B 11/18; G01B 11/22; G01B 11/24; G01B 11/245; G01D 5/268; G01D 5/353; G01D 5/35316; G01D 5/35354; G01D 5/35358; G01D 5/35361; G01D 5/35364; G01D 5/35367; G01D 5/3537; G01D 5/35374; G01D 5/3538; G01M 11/30; G01M 11/31; G01M 11/3109; G01M 11/3145; G01M 11/3172
USPC .............. 356/32, 35.5, 73.1, 601, 614, 634; 385/12, 13
See application file for complete search history.

(56) References Cited

U.S. PATENT DOCUMENTS

| | | | |
|---|---|---|---|
| 7,194,296 | B2 | 3/2007 | Frantz et al. |
| 7,813,599 | B2 | 10/2010 | Moore |
| 2002/0183592 | A1 | 12/2002 | Suzuki et al. |
| 2005/0261700 | A1 | 11/2005 | Tuma et al. |
| 2006/0013523 | A1 | 1/2006 | Childlers et al. |
| 2009/0217769 | A1 | 10/2009 | Roberts |
| 2010/0030063 | A1 | 2/2010 | Lee et al. |
| 2011/0202069 | A1 | 8/2011 | Prisco et al. |
| 2012/0203067 | A1 | 8/2012 | Higgins et al. |
| 2014/0061452 | A1 | 3/2014 | Schade |
| 2015/0305597 | A1* | 10/2015 | Ito .......................... G02B 23/26 600/424 |
| 2016/0047976 | A1 | 2/2016 | Schade et al. |
| 2017/0281049 | A1* | 10/2017 | Yamamoto ............. A61B 34/20 |
| 2017/0319049 | A1* | 11/2017 | Laby .................... A61B 1/0052 |
| 2018/0031493 | A1* | 2/2018 | Tojo .................... H04N 5/2256 |
| 2018/0078317 | A1* | 3/2018 | Mariampillai ......... A61B 34/20 |

FOREIGN PATENT DOCUMENTS

| | | | |
|---|---|---|---|
| DE | 102013205205 | A1 | 10/2014 |
| EP | 1593350 | B1 | 11/2005 |
| EP | 1961666 | B1 | 11/2012 |
| JP | 2002253481 | A | 9/2002 |
| WO | WO 0133165 | A1 | 5/2001 |
| WO | WO 2009097461 | A1 | 6/2009 |
| WO | WO 2011086432 | A2 | 7/2011 |
| WO | WO 2011100124 | A1 | 8/2011 |
| WO | WO 2012114224 | A1 | 8/2012 |
| WO | WO 2012158324 | A2 | 11/2012 |
| WO | WO 2013024418 | A1 | 2/2013 |
| WO | WO 2013057620 | A1 | 4/2013 |
| WO | WO 2013102827 | A1 | 7/2013 |
| WO | WO 2013173227 | A1 | 11/2013 |
| WO | WO 2013173229 | A1 | 11/2013 |
| WO | WO 2014053925 | A1 | 4/2014 |
| WO | WO 2014053941 | A1 | 4/2014 |

OTHER PUBLICATIONS

Fraunhofer Heinrich Hertz Institute, HHI FS Stryker 3D Sensing MAN, Fiber Optical Sensor Systems, 2013, 7 pages.
English language abstract and translation for JP2002253481 extracted from espacenet.com database Aug. 23, 2016, 19 pages.
English language abstract and machine-assisted translation for DE10100739 extracted from espacenet.com database Aug. 16, 2016, 7 pages.
Waltermann et al., Christian, "Femtosecond Laser Aided Processing of Optical Sensor Fibers for 3D Medican Navigation and Tracking (FiberNavi)," 23rd International Conference on Optical Fiber Sensors, Jun. 2, 2014, Proc. SPIE 9157, 4 pages.
Moore et al., Jason P., "Shape sensing using multi-core fiber optic cable and parametric curve solutions", Optics Express 2967, Jan. 30, 2012, vol. 20 No. 3, 7 pages.
Lee et al., Kenneth K.C., "Temperature-compensated fiber-optic 3D shape sensor based on femtosecond laser direct-written Bragg grating waveguides", Optics Express 24076, Oct. 7, 2013, vol. 21 No. 20, 11 pages.
English language abstract not found for DE102013205205. However, see English language equivalent U.S. 2016/047976.
English language abstract not found for DE102011017622. However, see English language equivalent U.S. 2014/061452.
English language abstract for EP1593350 extracted from espacenet.com database Aug. 23, 2016, 10 pages. Also see English language equivalent U.S. 2005/261700.
Olympus America, Scopeguide, Retrieved on Aug. 23, 2016, Retrieved from the Internet—http://medical.olympusamerica.com/technology/scopeguide.
Medtronic PLC, Interventional Lung Solutions, Retrieved on Aug. 23, 2016, Retrieved from the Internet—http://www.superdimension.com/.
Hansen Medical, Medical Robotics, Robotic Catheter, Retrieved on Aug. 23, 2016, Retrieved from the Internet—http://www.hansenmedical.com/us/.

* cited by examiner

SYSTEM AND METHOD FOR RECONSTRUCTING A TRAJECTORY OF AN OPTICAL FIBER

CROSS-REFERENCE TO RELATED APPLICATION

This application claims priority to European Patent Application 14 004 396.9, filed on Dec. 23, 2014, and entitled "System and Method for Reconstructing a Trajectory of an Optical Fiber" the complete disclosure of which is hereby incorporated herein by reference.

TECHNICAL FIELD

The present disclosure relates in general to reconstructing a trajectory of an optical fiber. The disclosure relates in particular to a system and a method for reconstructing a trajectory of an optical fiber which is inserted into an object.

BACKGROUND

Systems for tracking a position and an orientation of a rigid device in relation to an object and in relation to image data of the object are used in many types of applications. One application in which such systems are commonly used is in the field of optically navigated surgical procedures. In this case, the navigation of the rigid device is typically based on optical tracking (e.g., using visual markers rigidly attached to the device and an optical localization system detecting the visual markers).

In some applications it is desirable to track a flexible device (e.g., an endoscope, a catheter or a flexible needle) which is inserted into the object. In this case, the tracking of a shape of the flexible device within the object can become relevant in order to assist in executing a particular procedure. The tracking allows, for example, to improve the accuracy of a surgical procedure (to prevent erroneous steering of the flexible device) and to minimize the invasiveness thereof. One technology which is commonly used in this regard is the so-called fiber shape matching technology. This technology uses an optical fiber which is attached to or integrated in the flexible device to be tracked. A plurality of bending sensor units, such as fiber Bragg grating sensors, is arranged at different portions along a length of the optical fiber and provide bending information from said portions. By means of an interpolation of the bending information, the shape of the flexible device is reconstructed and may thus be tracked.

If the device is inserted into a highly curved and branched object, such as a tubular structure, a high number of bending sensor units needs to be arranged along the optical fiber to achieve sufficient reconstruction accuracy. To avoid the high number of bending sensor units, WO 2012/158324 A2 suggests reconstructing the shape of the flexible device by registering the bending information provided by a plurality of bending sensor units with a three-dimensional model of the object.

SUMMARY

There is a need for an improved solution for reconstructing a shape of a flexible device which is inserted into an object.

According to one aspect, a system for reconstructing a trajectory of an optical fiber which is inserted into an object is provided. The system comprises an optical fiber having a length and at least one bending sensor unit arranged along its length, a measurement device configured to measure insertion length increments of the optical fiber and an interrogation device configured to detect optical feedback signals from the at least one bending sensor unit. The system further comprises a processor device configured to reconstruct the trajectory of the optical fiber along its inserted length using data pairs which are based on measured insertion length increments and detected optical feedback signals assigned thereto.

In a first variant, the optical fiber has a proximal portion and one of one or more bending sensor units are arranged at the proximal portion of the optical fiber. Proximal may, in this regard, correspond to the part of the optical fiber to be first inserted into the object. If the optical fiber has a plurality of bending sensor units, the bending sensor units may be arranged at different positions along the length of the optical fiber. In this case, the bending sensor units may be spaced apart from each other by a distance of, for example, not less than 1 cm to 10 cm (e.g., 2 cm). In the case of more than two bending sensor units, each pair of adjacently arranged bending sensor units may be spaced apart from each other by the same distance or by varying distances. The number of bending sensor units arranged along the optical fiber may be between 1 and 50, especially between 3 and 20 (e.g., approximately 10).

The measurement device may be configured to measure the insertion length increments based on one or more of optical signals (e.g., using visual markers on the optical fiber and an optical system detecting the visual markers), electrical signals (e.g., using capacitive or resistive displacement sensors) and mechanical components (e.g., using a decoder wheel). The measured insertion length increments may correspond to changes of the insertion length between successive stages of the insertion.

The data pairs may be indicative of insertion lengths of the at least one bending sensor unit and detected optical feedback signals assigned thereto. In this case, the insertion lengths may be derived from the measured insertion length increments. The data pairs may be acquired on the basis of each of the measured insertion length increments and/or of each of the detected optical feedback signals. Alternatively, the data pairs may be acquired on the basis of a subset (i.e., less than all) of measured insertion length increments and detected optical feedback signals. In this case, the processor device may be configured to determine (e.g., select) the measured insertion length increments and detected optical feedback signals on which the data pairs are based.

The data pairs may be ordered. In this case, the ordering may be one-dimensional (e.g., based on the insertion length or based on time points assigned to different stages of the insertion) or two-dimensional (e.g., based on the insertion length and the time points).

A set of (e.g., ordered) data pairs may be defined by $$S_{pairs,m,n} = \{(R_{i,j}, L_{i,j}(\Delta I_1, \ldots \Delta I_i))\}, \text{ for } i=1, \ldots m, j=1, \ldots n \text{ and } L_{i,j} > 0,$$

where m is the number of length increment measurements considered in the data pairs, n is the number of bending sensor units, $R_{i,j}$ is the optical feedback signal detected from bending sensor unit j and assigned to the $i^{th}$ length increment measurement, $\Delta I_1, \ldots \Delta I_i$ are the insertion length increments as measured from the $1^{st}$ to the $i^{th}$ length increment measurement and $L_{i,j}$ is the determined insertion length of bending sensor unit j at the $i^{th}$ length increment measurement.

The optical fiber may have a proximal end (at the proximal part of the optical fiber) and the at least one bending sensor unit may be arranged at a predetermined distance from the proximal end. In this case, the insertion length of the at least one bending sensor unit is determined by $$L_{i,j}=I_i(\Delta I_1, \ldots \Delta I_i)-D_j, \text{ for } i=1, \ldots m, j=1, \ldots n$$
$$\text{and } I_i(\Delta I_1, \ldots \Delta I_i) > D_j,$$

where $D_j$ is the predetermined distance of bending sensor unit j from the proximal end of the optical fiber and $I_i$ is the insertion length of the optical fiber derived from the length increment measurements (e.g., by up-summing or integration of the insertion length increments $\Delta I_i$).

The processor device may be configured to reconstruct the trajectory (e.g., in terms of its shape) of the optical fiber during a phase of insertion of the optical fiber into the object and to (e.g., repeatedly) update the trajectory reconstruction as the insertion proceeds. In this case, the processor device may be configured to update the trajectory reconstruction on the basis of each one or more data pairs acquired at successive stages (e.g., at successive points in time) of the insertion.

The processor device may be further configured to reconstruct the trajectory of the optical fiber along its inserted length using an interpolation between the data pairs. The interpolation may, for example, be one of a linear, a cubic or a spline interpolation. In addition or as an alternative to this, the interpolation may be a model-based interpolation.

The processor device may be further configured to reconstruct the trajectory of the optical fiber using a weighted interpolation between the data pairs. In one implementation, the weighted interpolation gives more weight to data pairs acquired at a later stage of the insertion. In this case, the weighting may be performed during a movement in one direction (with a plurality of bending sensor units arranged along the optical fiber) and/or during a forward and backward movement of the optical fiber (with one or more bending sensor units arranged along the optical fiber). In another embodiment, the weighted interpolation may weigh the data pairs based on a quality of the optical feedback signal.

In addition or as an alternative to this, the processor device may be configured to detect a deviation between the trajectories reconstructed at successive stages of the insertion. The processor device may be configured to cause an activation of a signaling device when the detected deviation exceeds a predetermined threshold. The signaling device may be at least one of a visualization device (e.g., a monitor) or a device providing an alarm signal. The alarm signal may provide at least one of optic, acoustic and haptic feedback.

Each bending sensor unit may include at least two (e.g., three) strain sensors. The strain sensors may correspond to fiber Bragg gratings (FBG) sensors. Alternatively, the strain sensors may correspond to optical fiber sensors based on Rayleigh scattering effects or other strain sensor implementations. The optical feedback signals from the at least one bending sensor unit may include three-dimensional strain information of an optical fiber portion at which the bending sensor unit is arranged. The three-dimensional strain information may be transformed to a three-dimensional bending radius.

The system may further comprise a flexible instrument. The flexible instrument may, for example, correspond to a catheter, a flexible needle, an endoscope or a different minimalinvasive surgical device. The optical fiber may be included in the flexible instrument. In this case, the flexible instrument may, for example, have a channel into which the optical fiber is arranged or into which the optical fiber is inserted during the insertion of the instrument into the object. As an alternative to this, the optical fiber may be attached to the flexible instrument (e.g., at an outer side thereof). At least in the case, where the flexible instrument is arranged in the object, the insertion length increments of the optical fiber may be measured by means of insertion length increments of the instrument. For this purpose, a predetermined spatial relation between the instrument and the optical fiber may be evaluated.

The processor device may be configured to reconstruct a shape of the instrument based on the reconstructed trajectory of the optical fiber. In this case, the processor device may be configured to evaluate the predetermined spatial relation between the instrument and the optical fiber.

The processor device may be configured to register the trajectory of the optical fiber with image data of the object. In this case, the system may further comprise an imaging device configured to acquire image data of the object. In addition or as an alternative to this, the processor device may be configured to obtain and/or to store previously acquired image data. Based on the image data, the processor device may be further configured to calculate a model of a tubular structure of the object and to register the trajectory of the optical fiber with the model of the tubular structure. The trajectory of the optical fiber may be registered with the model of the tubular structure (e.g., by using shape matching and/or optimization algorithms). As an alternative to this, the processor device may be configured to register (superimpose) the trajectory of the optical fiber with image data of dense matter (e.g., brain or other tissue).

The system may further comprise a visualization device. The visualization device may, for example, correspond to a tablet display, a monitor or a printer. The processor device may be configured to control the visualization device to visualize at least the reconstructed trajectory of the optical fiber. Additionally, the processor device may be configured to control the visualization device to visualize image data of the object and/or the reconstructed shape of the flexible instrument. The processor device may be configured to control the visualization device to visualize at least the reconstructed trajectory during a phase of insertion of the optical fiber into the object and to update the visualization as the insertion proceeds.

The system may further comprise a tracking system. In this case, the processor device may be configured to track a position of the measurement device in relation to the object. For this purpose, a trackable device may be included in or may be attached to the measurement device. The tracking system may be an optical tracking system. The optical tracking system may, for example, comprise markers attached to the measurement device and a camera configured to detect the markers. As an alternative or in addition to this, the measurement device may be rigidly attached to the object and registered to the image data of the object.

The system may further comprise at least one sensor (e.g., a FBG sensor) arranged along the optical fiber which is configured to measure a physical property. The at least one sensor may be one of a (blood) pressure sensor, a temperature sensor, a (blood) flow sensor and a sensor for performing evanescence field spectroscopy. In an alternative to this, the interrogation device of the system may be configured to measure and evaluate light which is reflected from the tissue of the object adjoining the proximal end of the optical fiber.

According to a second aspect, a method for reconstructing a trajectory of an optical fiber which is inserted into an object is provided. The method is performed by a system, wherein the system comprises an optical fiber having a length and at least one bending sensor unit arranged along its length, a measurement device, and an interrogation device. The method comprises the steps of measuring, by the measurement device, insertion length increments of the optical fiber and detecting, by the interrogation device, optical feedback signals from the at least one bending sensor unit. The method further comprises the step of reconstructing the trajectory of the optical fiber along its inserted length using data pairs which are based on measured insertion length increments and detected optical feedback signals assigned thereto.

According to a third aspect, a computer program product is provided. The computer program product is stored on a computer-readable storage medium and is configured to cause a computer to execute the methods and method aspects disclosed herein when run on a processor of the computer.

BRIEF DESCRIPTION OF THE DRAWINGS

The above and other aspects and features of the system and method presented herein may be understood further with reference to the following description and drawings of exemplary arrangements.

DETAILED DESCRIPTION

Figure 1A:
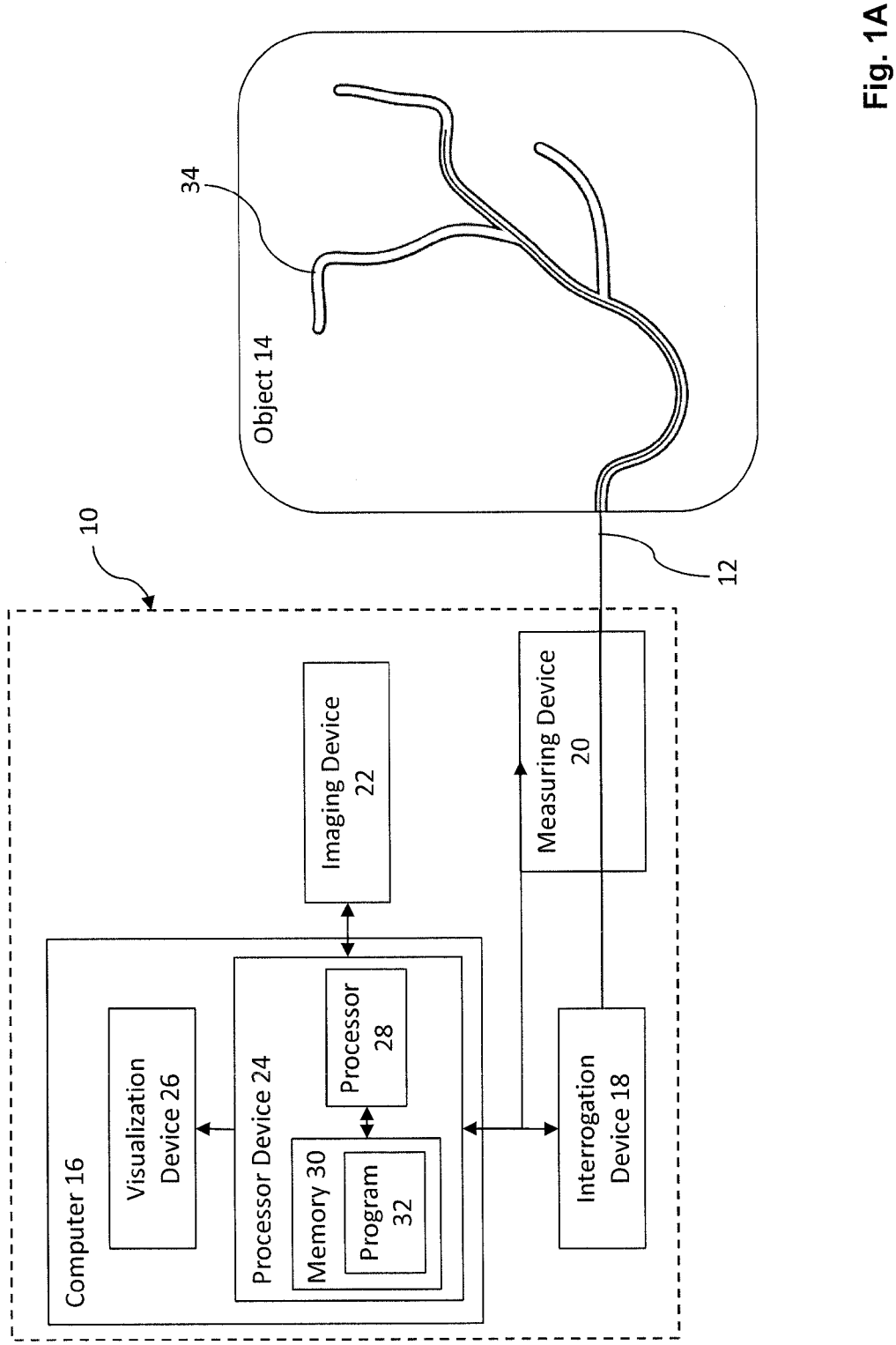
FIGS. 1A and 1B show schematic block representations of embodiments of a system for reconstructing a trajectory of an optical fiber which is inserted into an object.

FIG. 1A shows a block representation of a system, denoted in general by 10, for reconstructing a trajectory of an optical fiber 12 which is inserted into an object 14. The system 10 comprises a computer 16, an interrogation device 18, a measurement device 20 and an imaging device 22.

The optical fiber 12 extends from the interrogation device 18 through the measurement device 20 into the object 14. A length of the optical fiber 12 is described by its extension. In the present case, two bending sensor units (not shown) are arranged along the length of the optical fiber 12. In an alternative configuration, the optical fiber 12 may have more than two of bending sensor units or only one bending sensor unit arranged along its length. For example, the optical fiber 12 may have between one bending sensor unit and 50 bending sensor units, especially between 3 bending sensor units and 15 bending sensor units, arranged along its length.

The optical fiber 12 in the present embodiment is included in a flexible catheter (not shown) which is inserted into the object 14. For this purpose, a channel is incorporated in the catheter and the optical fiber 12 is arranged within the channel. Alternatively, the optical fiber 12 may be inserted into the channel of the catheter during its insertion into the object 14 or the optical fiber 12 may be attached to the catheter. The optical fiber 12 may further be included in or attached to an outside of a different flexible instrument (e.g., an endoscope or a flexible needle) or a rigid instrument, or it may constitute the instrument itself. In another embodiment, a guide wire for the instrument may be placed in the object prior to the instrument. In one variant, the optical fiber 12 may be included in, attached to or constitute the guide wire for the instrument. In yet another embodiment, the optical fiber 12 may not be assigned to an instrument.

In the embodiment shown in FIG. 1A, the optical fiber 12 (along with the instrument) is inserted into a tubular structure 34 within the object 14. The object 14 may, for example, be a patient. The tubular structure 34 may correspond to a vascular structure in different regions of the patient's body, such as a cardio structure, a vessel structure in the brain, a bronchi structure or a bowel. In a different embodiment, the optical fiber 12 may be inserted into tissue of the patient (e.g., brain tissue).

The interrogation device 18 is configured to induce an insertion of light into the optical fiber 12 and to measure the light which is reflected from the bending sensor units of the optical fiber 12. The interrogation device 18 is further configured to derive optical feedback signals based on the measured reflected light. In another embodiment, the interrogation device 18 may be integrated in the processor device 24 or may be incorporated in the instrument.

The measurement device 20 is configured to measure insertion length increments of the optical fiber 12 at different (e.g., successive) stages of the fiber insertion into the object 14. As an alternative or in addition to this, the measurement device 20 may be configured to measure total insertion lengths of the optical fiber 12 as the optical fiber 12 is inserted into the object 14.

The imaging device 22 is configured to capture two-dimensional and/or three-dimensional image data of the object 14. In the embodiment shown, the imaging device 22 is an MRI scanner allowing a high-resolution imaging of the tubular structure 34. In another embodiment, the imaging device 22 may be a different imaging device, such as a CT scanner, a PET scanner or one of a device for ultrasonic or X-ray fluoroscopy.

The computer 16 comprises a processor device 24 and a visualization device 26. The processor device 24 comprises at least one processor 28 (e.g., a central processing unit, CPU, or a graphics processing unit, GPU) and a computer-readable storage medium (memory) 30. The memory 30 is configured to store at least one computer program product (program) 32. The program 32 controls operations to be executed by the computer 16 (e.g., by the processor 28). The memory 30 may, for example, be a semiconductor memory, a solid state memory or a removable storage device. In the embodiment shown, the visualization device 26 corresponds to a computer monitor.

The processor device 24 interfaces with the interrogation device 18 and the measurement device 20. The processor device 24 is configured to generate data pairs which are based on the optical feedback signals determined by the interrogation device 18 and associated the insertion length increments of the optical fiber 12 measured by the measurement device 20 as determined at successive points in time. Using the data pairs, the processor device 24 is further configured to reconstruct a trajectory (including a shape) of the optical fiber 12 along its inserted length.

The processor device 24 may be further configured to reconstruct a shape of the catheter based on the reconstructed trajectory of the optical fiber 12. In this case, a spatial relation of the optical fiber 12 to the catheter may be predetermined and evaluated for catheter shape reconstruction.

The processor device 24 is configured to read previously acquired image data from the imaging device 22. The read image data may be stored in the memory 30 of the processor device 24. As an alternative or in addition to this, the processor device 24 may be configured to control the imaging device 22 to capture intra-operative image data when inserting the optical fiber 12 into the object 14. The processor device 12 may be configured to register the reconstructed trajectory of the optical fiber 12 (and/or the reconstructed shape of the catheter) with the image data of the object 14 (e.g., of the tubular structure 34)

The processor device 24 is configured to control the visualization device 26 to visualize the trajectory reconstruction of the optical fiber 12. As an alternative or in addition to this, the processor device 24 may be further configured to control the visualization device 24 to visualize at least one of the reconstructed shape of the instrument, the acquired image data of the object 14 (captured by the imaging device 22 and/or stored in the memory 30) and information with regard to the planned procedure of inserting the optical fiber 12 into the object 14.

Figure 1B:
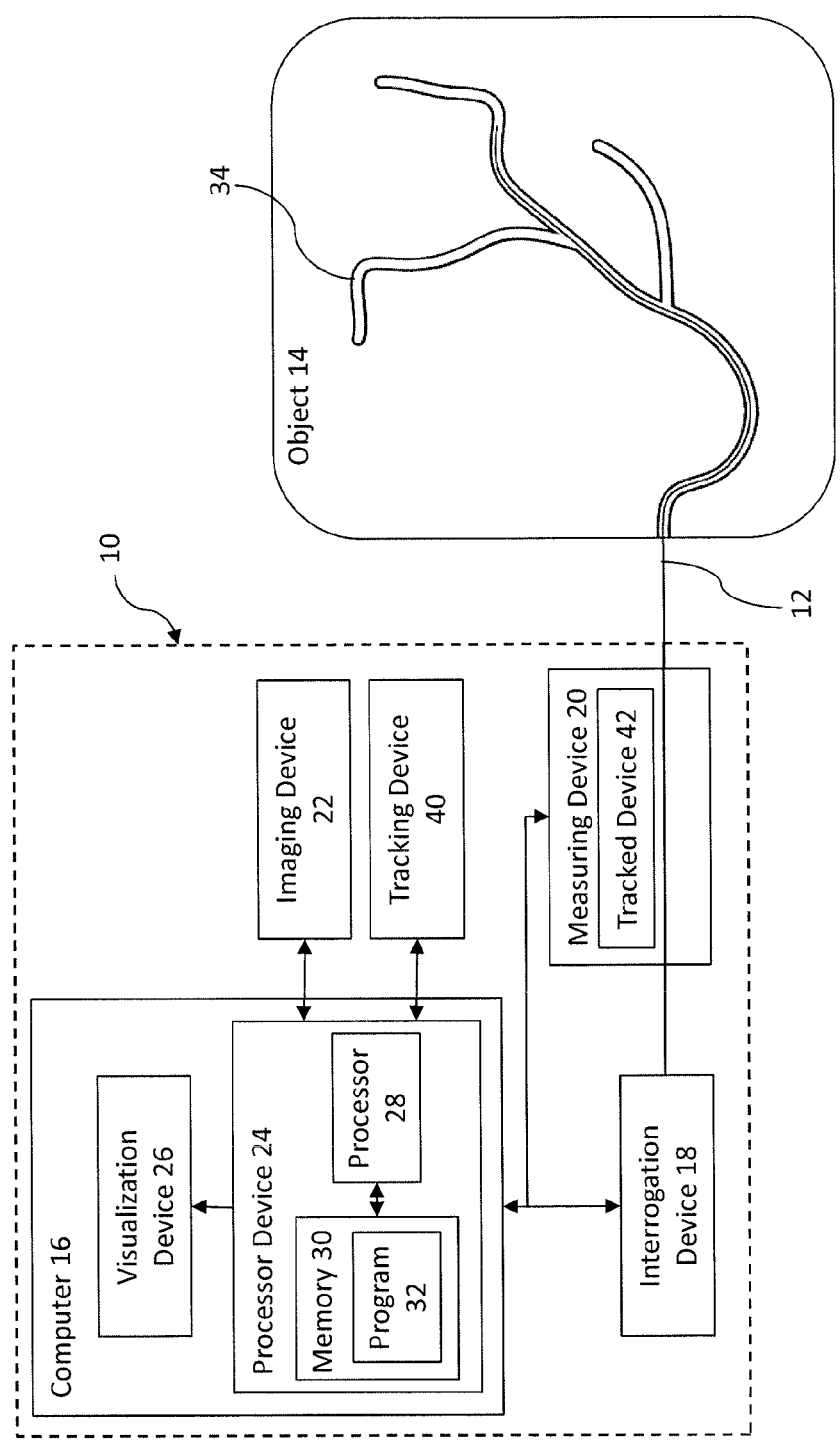

The system 10 according to FIG. 1B is similar to the system according to FIG. 1A, but additionally comprises a tracking system. The tracking system comprises a tracking device 40 which interfaces with the processor device 24 and a complementary tracked device 42 which has a predetermined spatial relation to the measurement device 20. In the embodiment shown, the tracking system is an optical tracking system. In this case, the tracking device 40 comprises a camera. The complementary tracked device 42 corresponds to an assembly of visual markers detectable by the camera of the tracking device 40. In another embodiment, the tracking system may be a different (e.g., optical or electromagnetic) tracking system. Alternatively or additionally, the measurement device 20 may be rigidly attached to the object 14. In this case, the measurement device 20 may be registered to the image data of the object 14. In yet another embodiment, the tracking system may be configured to track a position of at least one of the bending sensor units of the optical fiber 12 within the object 14. In this case, the tracked device 42 may be assigned to that least one bending sensor unit.

Figure 2:
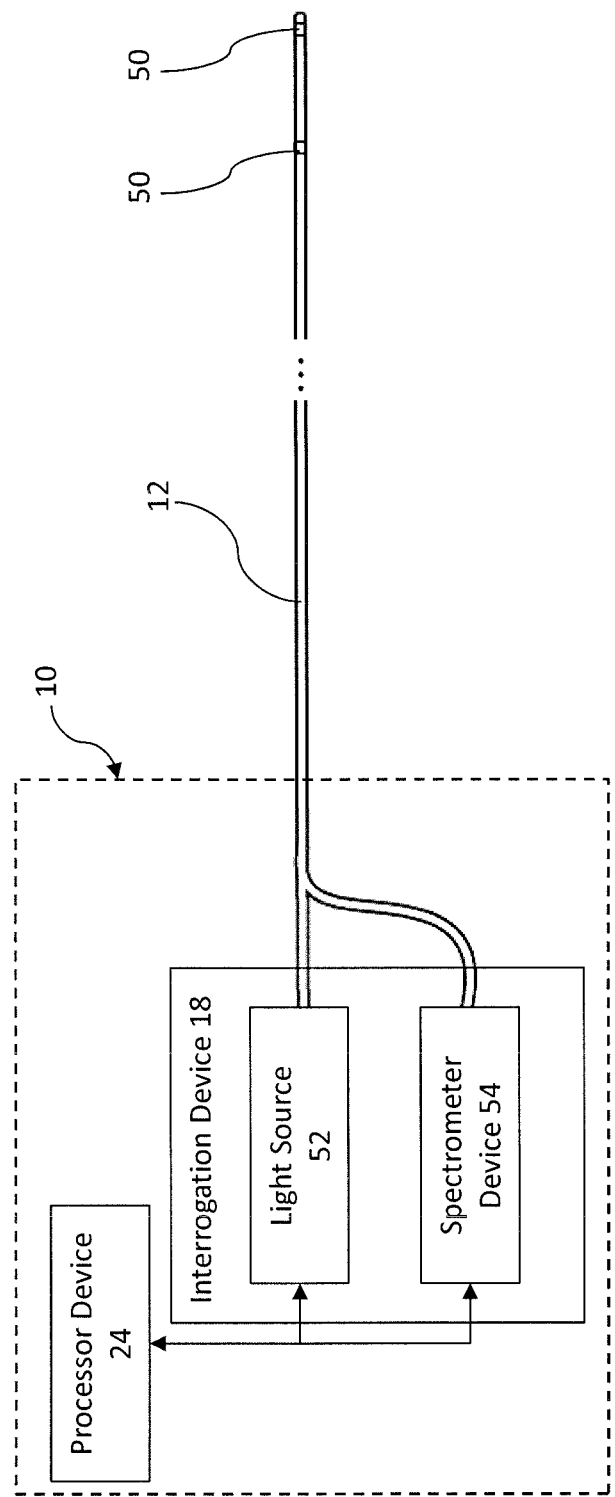
FIG. 2 shows a schematic representation of an embodiment of an interrogation device configured to detect optical feedback signals from an optical fiber.

FIG. 2 shows a schematic representation of an embodiment of an interrogation device 18, such as the interrogation device 18 of the system 10 according to FIGS. 1A and 1B. The interrogation device 18 is configured to detect optical feedback signals from the optical fiber 12 (cf. the embodiments according to FIGS. 1A and 1B). The optical fiber 12 may be a standard telecommunication fiber.

The optical fiber 12 has two (or more) bending sensor units 50 arranged along its length. The bending sensor units 50 are spaced apart from each other by a distance of about 2 cm. Alternatively, the two (or more) bending sensor units 50 are spaced apart from each other by a different distance (or varying distances), the distance being not less than 1 cm and/or not more than 10 cm.

In the embodiment shown in FIG. 2, the optical fiber 12 is a multi-core fiber including three fiber cores or includes three single-core fibers. Each bending sensor unit 50 comprises in the present embodiment three strain sensors which are assigned to the three fiber cores or the three single-core fibers, respectively. Such optical fibers 12 are, for example, described in U.S. Pat. No. 7,813,599 B2. In another embodiment, the optical fiber 12 may be a multi-core fiber including a different number of fiber cores (e.g., two fiber cores) and/or each bending sensor unit 50 may comprise a different number of strain sensors (e.g., two strain sensors). At least in the case of two strain sensors, the strain sensors may have temperature compensating properties or the optical fiber 12 may comprise means for temperature compansation. It may be further provided that the optical fiber 12 includes only one a single-core fiber. In this case, the strain sensors comprised by one of the bending sensor units 50 may be assigned to coupled microwaveguides branched from the fiber core. The latter technique is described in Waltermann et al., Femtosecond Laser Aided Processing of Optical Sensor Fibers for 3D Medical Navigation and Tracking (FiberNavi), Proc. SPIE 9157, 23rd International Conference on Optical Fiber Sensors, 91577G (Jun. 2, 2014).

The strain sensors of the bending sensor units 50 in the embodiment shown in FIG. 2 correspond to fiber Bragg grating (FBG) sensors. The FBG sensors are configured to reflect light of a sensor-specific wavelength (sensor-specific Bragg wavelength) and to transmit the remaining light. In dependence of a bending of the optical fiber 12, a shift is induced to the Bragg wavelengths reflected by the FBG sensors. In an alternative to this, the bending sensor units 50 may comprise other strain sensor types, such as based on Rayleigh scattering effects.

In another embodiment, alternative or additional sensors (e.g., FBG sensors) are arranged along the optical fiber 12 and configured to measure physical characteristics. The alternative or additional sensors may, for example, correspond to a pressure sensor (e.g., for blood pressure), a temperature sensor, a flow sensor (e.g., for blood flow) or a sensor for performing evanescence field spectroscopy (e.g., to detect molecules of interest or tissue characteristics). Alternatively, the interrogation device 18 may be configured to perform light spectroscopy. In this case, the interrogation device 18 may be configured to measure and evaluate the light transmitted through the optical fiber 12 and reflected from tissue of the object 14 (e.g., the patient) (cf. the embodiment according to FIGS. 1A and 1B).

The interrogation device 18 comprises a light source 52 and a spectrometer device 54. The light source 52 is connected to one end of each fiber core or fiber included in the optical fiber 12. The processor device 24 of the system 10 (cf. the embodiments according to FIGS. 1A and 1B) is configured to cause the light source 52 to emit light into the end of the fiber cores. The emitted light is transmitted along the length of the optical fiber 12 via total internal reflection. In the embodiment shown, the light source 52 is configured to emit light with a broad wavelength range, such as from about 1005 nm to about 1620 nm. In another embodiment, the light source 52 may correspond to a semiconductor laser having a tunable wavelength filter.

The spectrometer device 54 is configured to measure the wavelength reflected from each FBG sensor comprised by the bending sensor units 50. Under consideration of sensor-specific calibration data (e.g., stored in the memory 30 of the processor device 24 as described with regard to FIG. 1A), the spectrometer device 54 is configured to derive optical feedback signals. The optical feedback signals may be three-dimensional bending radii assigned to the portions of the optical fiber 12 at which the respective bending sensor units 50 are arranged. In another embodiment (e.g., in the case of a tunable light source), a light detection device different from the spectrometer device 54 is used, which is configured to measure the presence of reflected light. Such light detection device may, for example, be a photodiode.

Figure 3A:
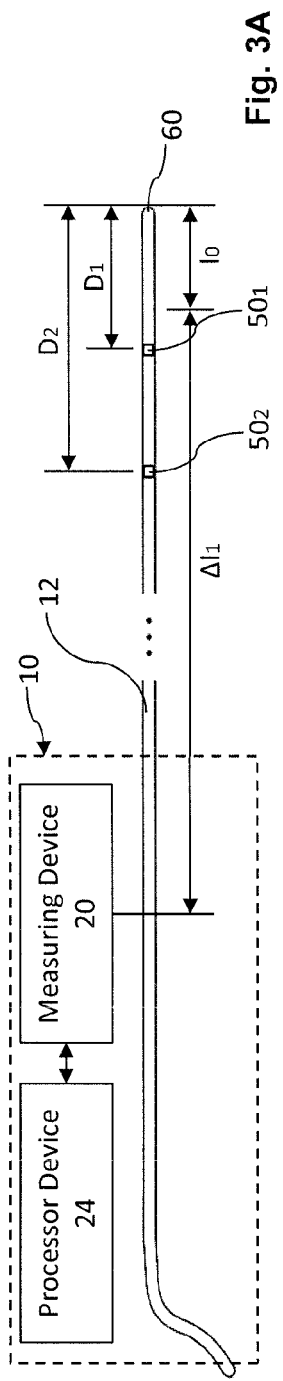
FIGS. 3A to 3C show schematic representations of embodiments of a measurement device configured to measure insertion length increments of an optical fiber.
Figure 3B:
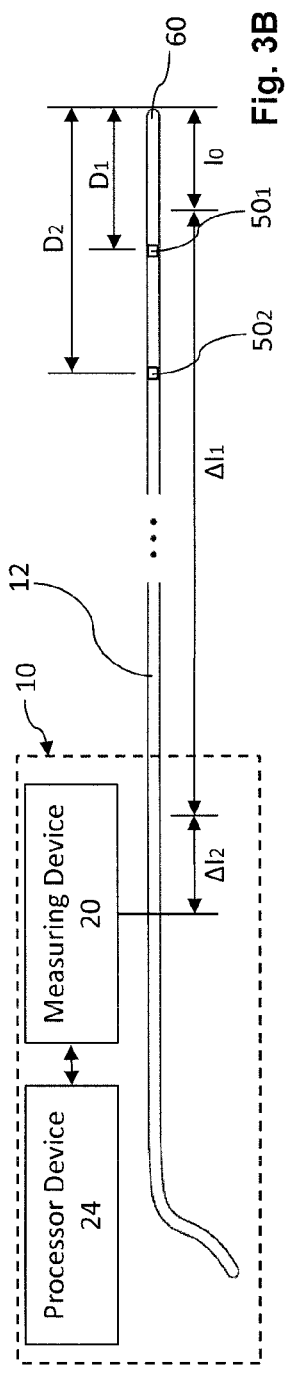
Figure 3C:
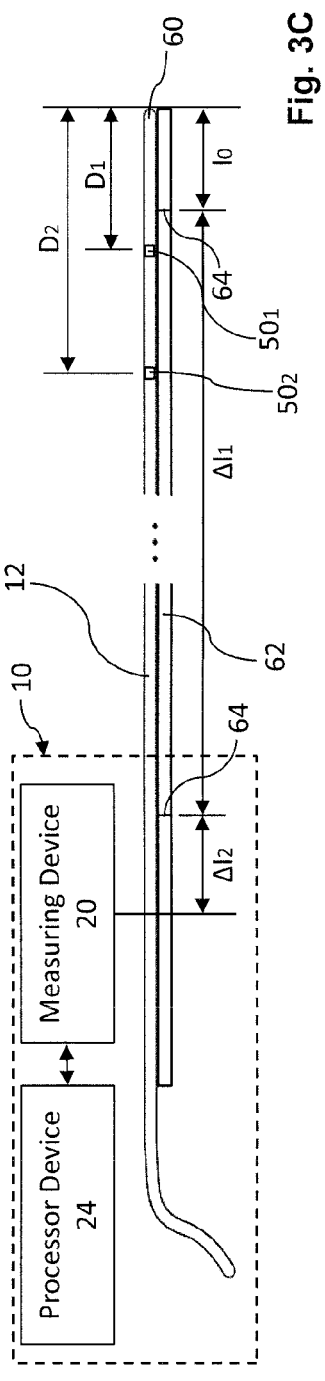

FIGS. 3A to 3C show a schematic representation of embodiments of a measurement device 20, such as the measurement device 20 of the system 10 according to FIGS. 1A and 1B. The measurement device 20 is configured to measure insertion length increments of the optical fiber 12 (cf. the embodiments according to FIGS. 1A to 2).

In the embodiment shown in FIGS. 3A and 3B, the measurement device 20 is configured to perform the measurements of the insertion length increments based on optical measurements. In this case, visual markers (not shown) are attached to the optical fiber 12. The visual markers are attached to positions along the length of the optical fiber 12 which correspond to positions of the bending sensor units 50 (as explained with regard to the embodiment shown in FIG. 2) or to different positions. The measurement device 20 comprises a camera (not shown) or another optical detector configured to detect the visual markers. In another embodiment, other optical measurements (e.g., based on reflections), electrical measurements (e.g., using capacitive or resistive displacement sensors) or mechanical measurements (e.g., using a decoder wheel) may be used to measure the insertion length increments.

The measurement device 20 is configured to measure insertion length increments of the optical fiber 12 by measuring changes of the insertion length at different stages of the insertion process. In another embodiment, the measurement device may be configured to repeatedly measure the total insertion length of the optical fiber 12 as the optical fiber 12 is moved into the object 14. The measurement device 20 may be configured to define a coordinate system and to locate the optical fiber 12 within the defined coordinate system. In this case, the defined coordinate system may be registered to image data of the object 14.

In the embodiment shown, the measurement device 20 is further configured to measure and/or to fix a rotation angle of the optical fiber 12 around its length during its insertion into the object 14 (cf. the embodiments according to FIGS. 1A and 1B). In another embodiment, a measurement and/or a fixation of the rotation angle of the optical fiber 12 may be performed by a different device (e.g., arranged in between the measurement device 20 and the object 14). The measurement of the rotation angle may be, for example, performed using visual markings on the outside of the optical fiber and a camera device detecting the rotation angle via the visual markings. In addition or as an alternative to this, the fixation of the rotation angle of the optical fiber 12 may be, for example, performed using a slotted sheathing of the optical fiber 12 which may be guided by a guiding structure such as a little pin.

The optical fiber 12 has a proximal end 60 which is the end of the optical fiber 12 that is to be inserted into the object 14. The two bending sensor units $50_1$ and $50_2$ exemplarily shown in FIGS. 3A and 3B are arranged at predetermined distances $D_1$ and $D_2$, respectively, from the proximal end 60 (or another point of interest) of the optical fiber 12. In the embodiment shown in FIGS. 3A and 3B, the bending sensor unit $50_1$ is arranged at a (proximal) portion of the optical fiber 12, which extends from the proximal end 60. Further, the bending sensor unit $50_2$ is arranged at a portion of the optical fiber 12 which is assigned to a larger distance $D_2$ to the proximal end 60 of the optical fiber 12 compared to $D_1$.

FIG. 3A schematically represents a first stage of the insertion process of the optical fiber 12 into the object 14. A reference insertion length $I_0$ is initially (i.e., prior to further inserting the optical fiber 12 into the object 14) measured by means of the measurement device 20, preconfigured (e.g., in the memory 30 according to FIGS. 1A and 1B), registered or arbitrary set. A first length increment $\Delta I_1$ is measured by means of the measurement device 20 with respect to the reference insertion length $I_0$ of the optical fiber 12. By means of a summation of the measured first length increment $\Delta I_1$ and the reference insertion length $I_0$, a first insertion length $I_1$ of the optical fiber 12 is derived.

FIG. 3B schematically represents a second stage of the insertion process, at which a second measured length increment $\Delta I_2$ of the optical fiber 12 is measured with respect to the first insertion length $I_1$. In general, an insertion length $I_i$ assigned to the $i^{th}$ length increment measurement is determined by $$I_i = I_{i-1} + I_i, \text{ for } i = 1, \ldots m,$$

where m is the number of the length increment measurements.

Based on the determined insertion length of the optical fiber 12, the processor device 24 (cf. the embodiments according to FIGS. 1A to 3B) or the measurement device 20 is configured to derive insertion lengths $L_1$ and $L_2$ of the bending sensor units $50_1$ and $50_2$, respectively, with respect to the reference position R. The insertion lengths of the bending sensor units $50_j$ are in general determined by $$L_{i,j} = I_i - D_j, \text{ for } i = 1, \ldots m, j = 1, \ldots n \text{ and } I_i > D_j,$$

where n is the number of the bending sensor units $50_j$.

The embodiment according to FIG. 3C is similar to the embodiment according to FIGS. 3A and 3B, but additionally comprises an instrument 62. The instrument 62 may correspond to the instrument 62 as described with regard to FIG. 1A. In the embodiment shown in FIG. 3C, the instrument 62 is rigidly attached to the optical fiber 12. In an alternative embodiment, the optical fiber may, for example, be inserted into the instrument 62.

In the embodiment of FIG. 3C, the measurement device 20 is configured to perform the measurements of the insertion length increments of the optical fiber 12 by means of measurements of the insertion length increments of the instrument 62. In this case, the spatial relation between the optical fiber 12 and the instrument 62 may be predetermined and known to computer 16. The measurement device 20 is configured to perform the measurements of the insertion length increments of the instrument 62 as described for the measurements of the insertion length increments of the optical fiber 12 with regard to FIGS. 3A and 3B. In the embodiment shown, visual markers 64 are attached to the instrument 62 in order to perform optical measurements. In an alternative to this, a visual pattern (e.g., a sticker) may be attached to the object 14 (cf. the embodiments according to FIGS. 1A and 1B). In this case, the measurement device 20 may comprise a camera or another optical detector configured to detect the instrument 62 and the visual pattern.

Figure 4C:
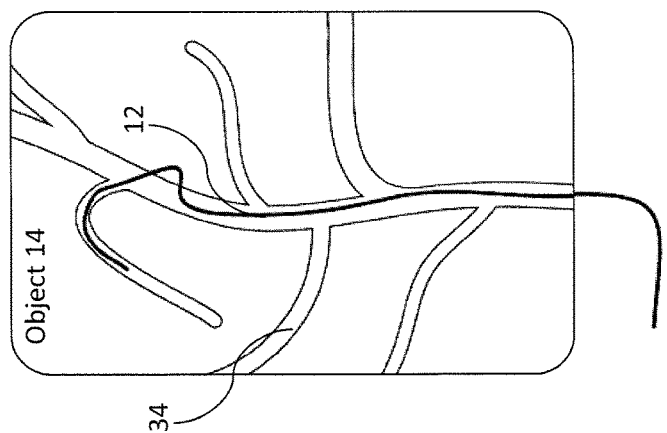
FIGS. 4A to 4C show schematic representations of reconstructed trajectories of an optical fiber which is inserted into an object.
Figure 4B:
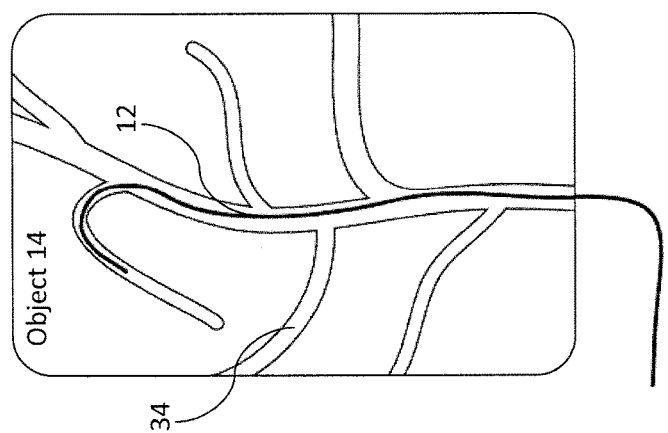
Figure 4A:
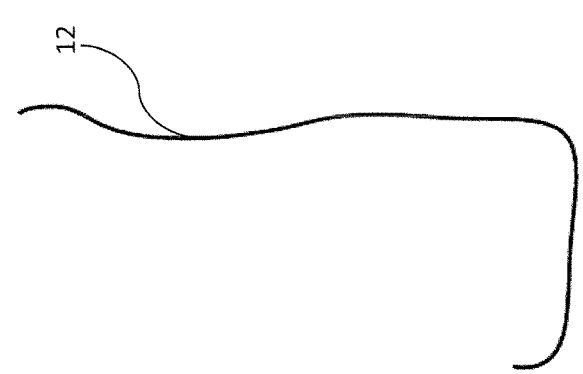

FIGS. 4A to 4C show schematic representations of reconstructed trajectories of the optical fiber 12 (cf. the embodiments according to FIGS. 1A to 3C) which is inserted into the tubular structure 34 of the object 14 (cf. the embodiments according to FIGS. 1A to 1B). As described with regard to FIGS. 1A and 1B, the processor device 24 of the system 10 is configured to perform the respective trajectory reconstructions.

The trajectory reconstructions according to FIGS. 4A to 4C correspond to different stages of the insertion of the optical fiber 12 into the tubular structure 34. Starting from the reconstructed trajectory shown in FIG. 4A and proceeding to the reconstructed trajectory shown in FIGS. 4B and 4C, insertion stages with increased insertion lengths of the optical fiber 12 within the tubular structure 34 are represented. For this purpose, the processor device 24 (cf. the embodiments according to FIGS. 1A to 3C) is configured to repeatedly update the trajectory reconstruction as the insertion of the optical fiber 12 into the tubular structure 34 proceeds. As such, FIGS. 4A to 4C may represent trajectory reconstructions of temporally successive stages of the insertion of the optical fiber 12 into the tubular system 34. In an alternative to this, the processor device 24 may be configured to reconstruct the trajectory after the insertion process of the optical fiber 12.

As described with regard to the embodiment shown in FIG. 1A, the processor device 24 is configured to control the visualization device 26 to visualize the reconstructed trajectory. In view of the reconstructions as shown in FIGS. 4A to 4C, the processor device 24 may be further configured to control the visualization device 26 to update the visualization as the insertion proceeds. In FIGS. 4B and 4C, the reconstructed trajectory of the optical fiber 12 superimposes image data of the tubular structure 34. The image data may be read by the processor device 24 from the imaging device 22 or the memory 30, as described with regard to the embodiment shown in FIG. 1A.

In FIG. 4C the reconstructed trajectory of the optical fiber 12 has a bulge which lies outside of the tubular structure 34. This may be caused by the optical fiber 12 being blocked within the tubular structure 34 or by the optical fiber 12 having passed the tubular structure 34. In an alternative to this, the bulge may be caused by a reconstruction error. In order to avoid such reconstruction error, the processor device 24 may be configured to use the image data for the trajectory reconstruction. In this case, reconstruction constraints may, for example, correspond to points in the image data which are expected to be passed by the optical fiber 12 when being inserted into the tubular structure 34.

Figure 5A:
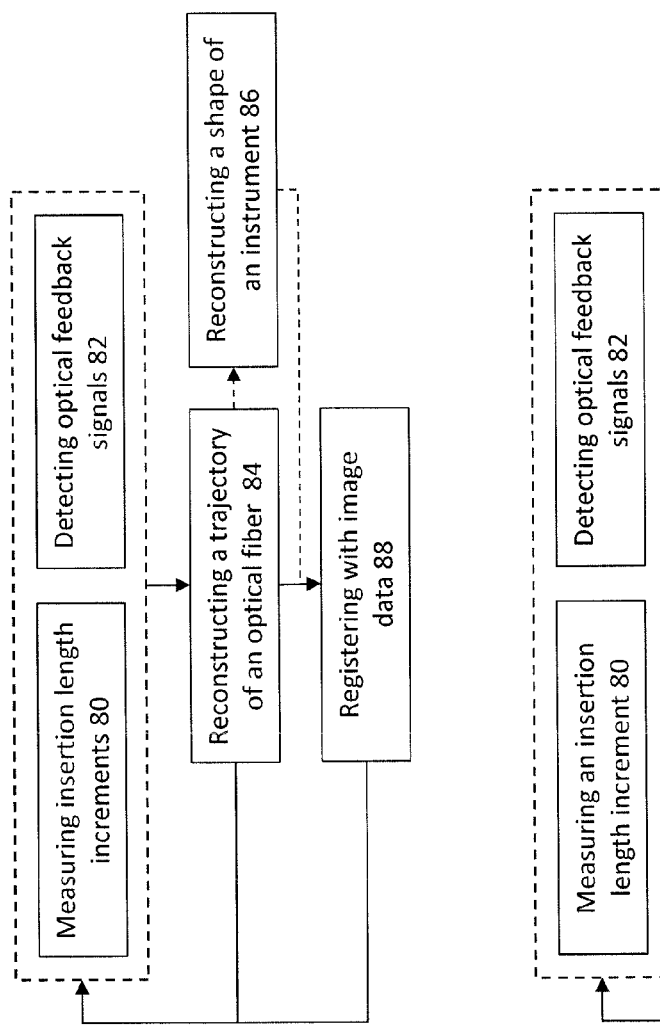
FIGS. 5A and 5B show flow diagrams of method embodiments for reconstructing a trajectory of an optical fiber which is inserted into an object.
Figure 5B:
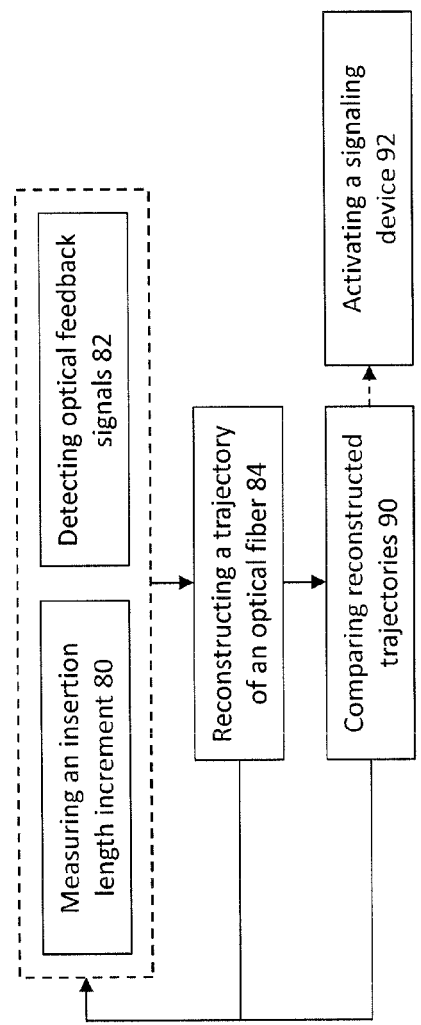

FIGS. 5A and 5B show flow diagrams of embodiments of a method for reconstructing the trajectory of the optical fiber 12 which is inserted into the object 14 (cf. the embodiments according to FIGS. 1A, 1B, 4B and 4C). The method may be performed by system 10 as explained with regard to the previously shown drawings.

In a first method step 80, an insertion length increment $\Delta I_i$ of the optical fiber 12 (and/or the instrument 62) is measured. The measurement may be performed by the measurement device 20 as described with regard to the embodiments shown in FIGS. 1A, 1B, 3A and 3C. In a second method step 82, optical feedback signals from the bending sensor units 50 (cf. the embodiments according to FIGS. 2 to 3C) are detected. In this case, the interrogation device 18, as explained with regard to the embodiments shown in FIGS. 1A to 2, may detect the reflected wavelength from each of the strain sensors included in the bending sensor units 50 and may be configured to derive optical feedback signals therefrom.

The measurement of the insertion length increment $\Delta I_i$ (step 80) and the detection of the optical feedback signals (step 82) may be synchronized (e.g., may both be performed at substantially the same point in time). In this case, the processor device 24 may be configured to perform the synchronization. In an alternative to this, the insertion of the optical fiber 12 (and the instrument 62) into the object 14 (cf. the embodiments according to FIGS. 1A, 1B, 4B and 4C) may be stopped after the measurement of the insertion length increment $\Delta I_i$ (step 80) until the detection of the optical feedback signals (step 82) has been performed.

In a next method step 84, the trajectory of the optical fiber 12 is reconstructed. In view of the embodiments described with regard to the previous drawings, the processor device 24 is configured to reconstruct the trajectory using data pairs which are based on the at least one measured insertion length increment (step 80) and the detected optical feedback signals (step 82) assigned thereto.

In this case, a set of data pairs is defined by $$S_{pairs,m\cdot n} = \{(R_{i,j}, L_{i,j}(I_i))\}, \text{ for } i=1, \ldots m, j=1, \ldots n \text{ and } L_{i,j} > 0,$$

where m is the number of length increment measurements (step 80) considered in the data pairs, n is the number of bending sensor units 50, $R_{i,j}$ is the optical feedback signal detected from bending sensor unit $50_j$ (step 82) and assigned to the $i^{th}$ length increment measurement, $I_i$ is the insertion length derived from the $i^{th}$ length increment measurement and $L_{i,j}$ is the determined insertion length of bending sensor unit $50_j$ at the $i^{th}$ length increment measurement (as described with regard to the embodiment shown in FIGS. 3A to 3C).

The data pairs may be ordered data pairs. In this case, the processor device 24 according to the embodiments shown in FIGS. 1 to 3C may be configured perform the ordering. The ordering may be one-dimensional, such as based on the insertion length or based on time points assigned to different stages of the insertion, or two-dimensional, such as based on the insertion length and the time points.

In the embodiments shown in FIGS. 5A and 5B, the reconstruction (steps 84) is based on the data pairs which were acquired on the basis of each of the measured insertion length increments (step 80) and each of the detected optical feedback signals (step 82). At least in this case, steps 80 and 82 are performed in a substantially simultaneous and synchronized manner. Alternatively, the data pairs may be acquired on the basis of a subset (i.e., less than all) of measured insertion length increments (step 80) and/or a subset (i.e., less than all) of detected optical feedback signals (step 82). In this case, the processor device 24 may be configured to determine (i.e., select) the measured insertion length increments and detected optical feedback signals on which the data pairs are based. The processor device 24 may, for example, be configured to base the selection on a curvature of the object 14 (e.g., provided by image data of the object 14).

Applied to the embodiments according to FIGS. 1A and 1B, the processor device 24 is configured to perform the trajectory reconstruction (step 84) using an interpolation between the data pairs. The trajectory (Traj) assigned to the $m^{th}$ length increment measurement is defined by $$\text{Traj}(m) = f_{Traj}(S_{pairs,m\cdot n}),$$

where $f_{Traj}$ describes the interpolation function. The interpolation may be, for example, implemented as a linear, a cubic or a spline interpolation. In addition or as an alternative to this, the interpolation may be a model-based interpolation. In this case, the interpolation may be based on constraints assigned to the material of the instrument 62 (cf. the embodiment according to FIG. 3C) (e.g., a maximal bending radius of the instrument 62) or to the tubular structure 34 (cf. the embodiments according to FIGS. 1A, 1B, 4B and 4C). Further interpolation techniques are described in U.S. Pat. No. 7,813,599 B2. In view of the embodiment as described with regard to FIGS. 3A and 3C, the processor device 24 may be further configured to consider the insertion angle of the optical fiber 12 (and the instrument 62) in the reconstruction of the trajectory Traj.

As described with regard to the embodiments shown in FIGS. 1A to 4C, a plurality of bending sensor units 50 is arranged along the length of the optical fiber 12. In this case, for each measured length increment (step 80) considered in the data pairs, optical feedback signals assigned to a plurality of insertion lengths are provided by the interrogation device 18. At least in this case, the processor device 24 may be configured to reconstruct the trajectory of the optical fiber 12 (step 84) using a weighted interpolation between the data pairs. The weighted interpolation may give more weight to data pairs acquired at a later stage of the insertion. In this way, the weighted interpolation may consider changes which occur in the trajectory of the optical fiber 12 within the object 14 during the insertion (e.g., due to erroneous steering). Alternatively, the weighted interpolation may weight the data pairs based on a quality of the optical feedback signal.

In another embodiment, the processor device 24 may be provided to be configured to reconstruct the trajectory of an optical fiber using a weighted interpolation between the data pairs although the optical fiber has only one bending sensor unit 50 arranged along its length. Also in this case, the weighted interpolation may give more weight to data pairs acquired at a later stage of the insertion, such as during a forward and backward movement of the optical fiber within the object 14 (cf. FIGS. 1A, 1B, 4B and 4C).

In the embodiment shown in FIGS. 5A and 5B, the processor device 24 (cf. the embodiments according to FIG. 1A to 3C) is configured to update the trajectory reconstruction (step 84) on the basis of each of the at least one data pair acquired at successive stages of the insertion (based on steps 80, 82). In this case, the processor device 24 be configured to update the trajectory reconstruction (step 84) after each of successive stages of the insertion or after a plurality of successive stages.

In a next (optional) method step 86, the shape of the instrument 62, as explained with regard to the embodiment shown in FIGS. 1A and 3C, is reconstructed. In this case, a spatial relation of the instrument 62 and the optical fiber 12 included in the instrument 62 is predetermined (calibrated). The processor device 24 is configured to reconstruct the shape of the instrument 62 (step 86) based on the reconstructed trajectory of the optical fiber 12 (step 84) and an evaluation of the predetermined spatial relation between the optical fiber 12 and the instrument 62.

In a following method step 88, the reconstructed trajectory of the optical fiber 12 (step 84) and (optionally) the reconstructed shape of the instrument 62 (step 86) is registered with image data of the object 14. For this purpose, the processor device 24 may be configured to read image data of the tubular structure 34 of the object 14 from the imaging device 22 or the memory 30 (cf. the embodiments as shown in FIGS. 1A and 1B). In this case, the processor device 24 may be configured to perform a segmentation of the tubular structure 34 and to calculate a (projected) two-dimensional model and/or a three-dimensional model (e.g., a voxel representation or a surface model) of the tubular structure 34 based on the performed segmentation. It may be further provided that the processor device 24 is configured to register the reconstructed trajectory of the optical fiber 12 and (optionally) the reconstructed shape of the instrument 62 to the model of the tubular structure 34 (step 88). The registration may, for example, be performed by matching the reconstructed trajectory to the model of the tubular structure 34 by state of the art shape matching/optimization algorithms. In addition or as an alternative to this, a point-by-point registration method may be used. In this case, a user may be enabled to select points (e.g., by means of the computer 16 as described in regard to FIG. 1A) in the image data of the tubular structure 34 which has been passed by the instrument 62 during the insertion process.

Unlike the embodiment as shown in FIG. 5A, in the embodiment of the method shown in FIG. 5B, the reconstructing of the trajectory of the optical fiber 12 (step 84) is followed by comparing reconstructed trajectories of different stages of the insertion process in method step 90 so as to detect a deviation there between. Applied to the embodiments as described with regard to FIGS. 1A to 3C, the processor device 24 may be configured to calculate an error function as described by Error(Traj($m$),Traj($m-x$)).

The processor device 24 is configured to compare the trajectories (Trap reconstructed at directly successive insertion stages (x=1) and/or of not directly successive intersection stages (x>1).

In a last (optional) method step 92, a signaling device is activated. The processor device 24 (cf. the embodiments according to FIGS. 1A to 3C) may be configured to activate a signaling device when the comparing of reconstructed trajectories (step 90) indicates a deviation that exceeds a predetermined threshold. The signaling device may, for example, be one of a device providing an alarm signal (e.g., a speaker or a flasher) and the visualization device 26 (cf. the embodiments according to FIGS. 1A and 1B). Also haptic feedback may be provided (e.g., via the instrument to which the optical fiber 12 is attached).

In view of the embodiments as described above, the trajectory of the optical fiber 12 and thus the shape of a flexible instrument may be reconstructed within an arbitrary object, such as the highly curved and branched tubular structure 34 (cf. the embodiments according to FIGS. 1A, 1B, 4B and 4C). For this purpose, only a small number of bending sensor units 50 (e.g., one bending sensor unit 50 or two bending sensor units 50) is necessary so as to achieve sufficient reconstruction accuracy. This advantage results from the possibility to individually control the reconstruction accuracy, such as the resolution, by controlling the size of the length increments.

The invention claimed is:

1. A system for reconstructing a trajectory of an optical fiber which is inserted into an object, comprising:
    an optical fiber having a length and at least one bending sensor unit arranged along its length;
    a measurement device configured to measure insertion length increments of the optical fiber;
    an interrogation device configured to detect optical feedback signals from the at least one bending sensor unit; and
    a processor device configured to reconstruct the trajectory of the optical fiber along its inserted length using data pairs which are based on the measured insertion length increments and the detected optical feedback signals assigned thereto.

2. The system of claim 1, wherein the data pairs are indicative of insertion lengths of the at least one bending sensor unit and detected optical feedback signals assigned thereto, the insertion lengths being derived from the measured insertion length increments.

3. The system of claim 2, wherein a set of the data pairs is defined by $$S_{pairs,m\cdot n} = \{(R_{i,j}, L_{i,j}(\Delta I_1, \ldots, \Delta I_i))\}, \text{ for } i=1, \ldots$$
$$m, j=1, \ldots n \text{ and } L_{i,j} > 0;$$

where R is the detected optical feedback signal, $\Delta I$ is the measured insertion length increment, L is the determined insertion length for an individual bending sensor unit, m is the number of length increment measurements considered in the data pairs and n is the number of bending sensor units.

4. The system of claim 2, wherein the optical fiber has a proximal end and the at least one bending sensor unit is arranged at a predetermined distance from the proximal end; and wherein the current insertion length of the at least one bending sensor unit is determined by $$L_{i,j}=I_i(\Delta I_1, \ldots, \Delta I_i)-D_j, \text{ for } i=1, \ldots m, j=1, \ldots n$$
$$\text{and } I_i>D_j;$$

where L is the currently determined insertion length for an individual bending sensor unit, $\Delta I$ is the measured insertion length increment, I is the insertion length of the optical fiber, D is the predetermined distance, m is the number of length increment measurements considered in the data pairs and n is the number of bending sensor units.

5. The system of claim 1, wherein the processor device is configured to reconstruct the trajectory of the optical fiber during a phase of insertion of the optical fiber into the object and to update the trajectory reconstruction as the insertion proceeds.

6. The system of claim 1, wherein the processor device is configured to reconstruct the trajectory of the optical fiber along its inserted length using an interpolation between the data pairs.

7. The system of claim 1, wherein the processor device is configured to reconstruct the trajectory of the optical fiber along its inserted length using a weighted interpolation between the data pairs.

8. The system of claim 7, wherein the weighted interpolation gives more weight to data pairs acquired at a later stage of the insertion of the optical fiber into the object.

9. The system of claim 1, wherein the optical fiber has a plurality of bending sensor units arranged along its length; and wherein the processor device is further configured to reconstruct the trajectory of the optical fiber at different stages of insertion, compare the trajectories reconstructed at successive stages of the insertion, and detect a deviation therebetween.

10. The system of claim 1, wherein the at least one bending sensor unit includes at least two fiber Bragg grating sensors.

11. The system of claim 1, wherein the optical feedback signals from the at least one bending sensor unit are or include three-dimensional strain information of an optical fiber portion at which the bending sensor unit is arranged.

12. The system of claim 1, wherein the system further comprises a flexible instrument; and wherein the optical fiber is included in or is attached to the flexible instrument.

13. The system of claim 12, wherein the insertion length increments of the optical fiber are measured by means of insertion length increments of the instrument.

14. The system of claim 12, wherein the processor device is further configured to reconstruct a shape of the instrument based on the reconstructed trajectory of the optical fiber.

15. The system of claim 1, wherein the processor device is further configured to register the trajectory of the optical fiber with image data of the object.

16. The system of claim 15, wherein the processor device is further configured to calculate a model of a tubular structure of the object based on the image data and to register the trajectory of the optical fiber with the model of the tubular structure.

17. The system of claim 1, further comprising a visualization device; and
wherein the processor device is further configured to control the visualization device to visualize at least the reconstructed trajectory of the optical fiber.

18. The system of claim 1, further comprising a tracking system; and wherein the processor device is further configured to track a position of the measurement device in relation to the object.

19. The system of claim 1, further comprising at least one sensor arranged along the optical fiber which is configured to measure a physical property.

20. The system of claim 19, wherein the at least one sensor is one of a pressure sensor, a temperature sensor, a flow sensor and a sensor for performing evanescence field spectroscopy.

21. A method for reconstructing a trajectory of an optical fiber which is inserted into an object, the method being performed by a system, wherein the system comprises an optical fiber having a length and at least one bending sensor unit arranged along its length, a measurement device and an interrogation device, the method comprising the steps of:
by the measurement device, measuring insertion length increments of the optical fiber;
by the interrogation device, detecting optical feedback signals from the at least one bending sensor unit; and
reconstructing the trajectory of the optical fiber along its inserted length using data pairs which are based on the measured insertion length increments and the detected optical feedback signals assigned thereto.

22. A method for reconstructing a trajectory of an optical fiber which is inserted into an object, the method being performed by a computer program product stored on a non-transitory computer-readable storage medium, said method comprising the steps of:
receiving data from a measurement device with the data indicative of insertion length increments of the optical fiber;
receiving data from at least one bending sensor unit with the data indicative of optical feedback signals detected with an interrogation device; and
reconstructing the trajectory of the optical fiber along its inserted length using data pairs which are based on the data indicative of the measured insertion length increments and the data indicative of the detected optical feedback signals assigned thereto.

* * * * *